United States Patent [19]

Shinagawa et al.

[11] 3,952,567
[45] Apr. 27, 1976

[54] GAS SENSOR

[75] Inventors: Kiminari Shinagawa, Hachioji; Sadao Hishiyama, Sayama; Shinichi Ito, Kokubunji; Kunifusa Kayama, Tokyo; Satoshi Taniguchi, Tokorozawa, all of Japan

[73] Assignee: The Hitachi Heating Appliances Co., Ltd., Kashiwa, Japan

[22] Filed: June 13, 1975

[21] Appl. No.: 586,813

[30] Foreign Application Priority Data
June 14, 1974  Japan................................ 49-67125

[52] U.S. Cl. ................................ 73/23; 23/254 E; 338/34
[51] Int. Cl.² ........................................ G01N 27/04
[58] Field of Search............ 23/254 E; 73/23, 27 R; 324/71 S, 71 N; 338/34; 340/237 R

[56]  References Cited
UNITED STATES PATENTS
3,603,954  9/1971  Takeuchi ................................ 73/23
3,772,908  11/1973  Kasahara ................................ 73/27

Primary Examiner—Herbert Goldstein
Attorney, Agent, or Firm—Stewart and Kolasch, Ltd.

[57]  ABSTRACT

A gas sensor comprising as a gas sensible material a spinel-type ferrite represented by the general formula $AFe_2O_4$ in which A stands for at least one member selected from the group consisting of Li, Mg, Mn, Fe, Co, Ni, Cu, Zn and Pb is provided. In many cases, a catalyzer or a recovering agent need not be incorporated in this gas sensor, and it is characterized in that it is hardly influenced by moisture in the atmosphere.

8 Claims, 10 Drawing Figures

GAS SENSOR

BACKGROUND OF THE INVENTION

1. Field of the Invention

This invention relates to a gas sensor. More particularly, the invention relates to a gas sensor for detection of reducing gases contained in air, exhaust gas, expired air or other test gases, such as hydrocarbons and their derivatives, e.g., propane, methane, butane, ethylene, alcohols, carbon monoxide, hydrogen, carboxylic acids and amines.

2. Description of the Prior Art

Detection of reducing gases contained in air, exhaust gas and expired air, such as mentioned above, has heretofore been conducted according to various methods, for example, gas chromatography, chemical analysis and nondispersive infrared absorption analysis. These methods, however, are defective in various points. For example, a large and expensive apparatus should be used, or experiences and skills are required for measurement or maintenance of measurement equipment. As means capable of overcoming these defects, there has been proposed a gas sensor comprising a material, the electric resistance of which changes greatly when it falls in contact with a reducing gas such as mentioned above. A so-called reduction-type oxide semiconductor such as $SnO_2$, ZnO and $Fe_2O_3$ is generally used as the gas sensible material in the gas sensor of this type. In many cases, in order to improve the response characteristics or the sensitivity in these gas sensors, a catalyzer is incorporated, and further, a recovering agent is added to restore the electric resistance after the measurement to the original electric resistance before the measurement.

These conventional gas sensors comprising a reduction-type oxide semiconductor such as mentioned above are advantageous over the above-mentioned conventional detection techniques in that they are very cheap and the measurement can be accomplished very easily when they are used. However, incorporation of a catalyzer or a recovering agent is indispensable for the reasons set forth above. Further, the sensitivity or restorability of the gas sensor varies greatly according to the kind or amount of the catalyzer or recovering agent. Therefore, it is very difficult to obtain gas sensors having certain uniform characteristics, and application fields of the gas sensor of this type are limited.

In addition, the above-mentioned gas sensor comprising a reduction-type oxide semiconductor is defective in that the value of the electric resistance is greatly influenced by moisture in the atmosphere and an erroneous operation is often caused by the change of the humidity. Accordingly, an improvement is desired in this connection also.

SUMMARY OF THE INVENTION

It is a primary object of this invention to provide a gas sensor having a high reliability which can overcome the foregoing defects involved in the conventional gas sensors and in which incorporation of a catalyzer or recovering agent is unnecessary in many cases and the sensitivity is hardly influenced by moisture contained in the atmosphere with no fear of an erroneous operation.

In this invention, the foregoing object is attained by using as a gas sensible material of a gas sensor a ferrite having a spinel-type crystal structure and a composition substantially represented by the general formula $AFe_2O_4$ in which A stands for at least one member selected from the group consisting of Li, Mg, Mn, Fe, Co, Ni, Cu, Zn and Pb.

DESCRIPTION OF THE PREFERRED EMBODIMENTS

Figure 1:
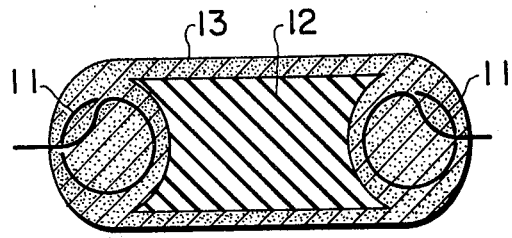
FIG. 1 and FIG. 2 are diagrams illustrating structures of gas sensors.
Figure 2:
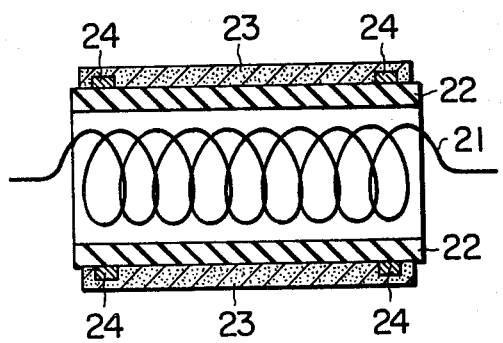

Various types of gas sensors comprising a material, the electric resistance of which greatly changes on contact with a reducing gas, have heretofore been proposed, and most of gas sensors of this type have, in general, a structure as shown in FIG. 1 or FIG. 2. When the measurement is conducted by using such conventional gas sensor, the oxygen-vacant type material is maintained at a certain temperature in the range of from 300°–500°C. and is contacted with a sample gas, the change of the electric resistance of the oxygen-vacant type material caused by the contact is determined and the reducing gas is detected or its content is calculated based on the determined value.

In a gas sensor having a structure as shown in FIG. 1, an oxygen-vacant type material 13 is coated on a spacer 12 composed of an insulating material such as alumina, and the change of the electric resistance of the oxygen-vacant type material 13 is measured by coil electrodes 11 fixed in the vicinity of both the ends of the spacer 12. A current is passed through the electrodes 11 from the outside, and the electrodes 11 have not only the function of measuring the electric resistance but also the function of maintaining the oxygen-vacant type material at a desired temperature.

In a gas sensor having a structure as shown in FIG. 2, an oxygen-vacant type material 23 is coated on the periphery of an insulating pipe 22 composed of alumina, and electrodes 24 are disposed at both the ends of the insulating pipe 22 to measure the electric resistance of the oxygen-vacant type material 23. A heater 21 is inserted into the interior of the insulating pipe 22 to maintain the gas sensor at a desired temperature.

As the oxygen-vacant type material for the above-mentioned type gas sensor, there have heretofore been used reduction-type semiconductors such as $SnO_2$ and their compositions including minute amounts of catalyzers or recovering agents. However, it is difficult to obtain oxygen-vacant type materials having uniform characteristics, and these conventional oxygen-vacant materials are highly sensitive to moisture contained in a sample gas and the sensitivity to a reducing gas to be detected is degraded by the presence of moisture. Accordingly, they are defective in that erroneous operations are readily caused and the reliability is very low.

In contrast, a spinel-type ferrite having a composition of the above general formula shows a high and prompt response to a minute amount of a reducing gas, and in many cases, incorporation of a catalyzer or recovering agent is unnecessary. Further, the electric resistance is hardly changed by the presence of moisture (humidity) and hence, the sensitivity to a reducing gas is not influenced. This invention has now been completed based on this novel finding. In short, according to this invention, there is provided a gas sensor which can overcome all of the foregoing defects involved in the conventional gas sensors and which has very excellent properties.

Figure 3:
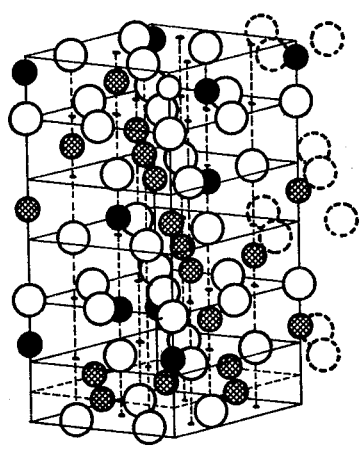
FIG. 3 is a model diagram illustrating the spinel-type crystal structure.

The spinel-type ferrite to be used in this invention is represented by the general formula $AFe_2O_4$ and has a crystal structure shown in FIG. 3. In FIG. 3, in the case of the normal spinel structure, marks ○, ●, and ⊜ denote oxygen, A and Fe, respectively, and in the case of the inverse spinel structure, marks ○, ●, and ⊕ denote oxygen, Fe and (A, Fe), respectively. As is apparent from FIG. 3, the unit cell of the spinel crystal structure consists of $^8A^{2+} \cdot {}^{16}Fe^{3+} \cdot {}^{32}O^{2-}$.

The mechanism in which the spinel-type ferrite detects a reducing gas has not been completely elucidated, but it is believed that when the spinel-type ferrite falls in contact with a reducing gas, the amount of oxygen vacancy in the oxide material is changed, resulting in the change of the valence of iron, namely the change of $Fe^{3+}$ to $Fe^{2+}$, and the electric resistance is also changed by this change of the valence of iron. It is also construed that this reaction is readily advanced in the spinel-type crystal structure.

Accordingly, for the gas sensor, it is important and indispensable that the crystal structure of the oxygen-vacant type material should be of the spinel type and that it should contain iron as one of the component elements.

In addition to the spinel-type ferrite, there are present a variety of ferrites, for example, perovskite-type ferrites, garnet-type ferrites and magnetoplumbite type ferrites. However, even if ferrites other than the spinel-type ferrite are contacted with a reducing gas, the electric resistance is not changed at all or it is hardly changed, or if the electric resistance be changed, the sensitivity is greatly influenced by moisture. Accordingly, these ferrites other than the spinel-type ferrite can hardly be used as a gas sensible material of a gas sensor.

In the gas sensor of this invention, since the change of the valence of iron is utilized as pointed out hereinabove, the presence of iron is indispensable. Accordingly, oxides having a spinel structure but being free of iron, for example, $NiMnO_4$, cannot be used as a gas sensible material of a gas sensor.

As is apparent from the foregoing, only ferrites having a spinel-type crystal structure or composition represented by the general formula $AFe_2O_4$ can be used in this invention. In the above general formula, A stands generally for a divalent metal element, and metal elements capable of linking with $Fe_2O_3$ to form a spinel-type ferrite of the above general formula, namely metal elements, that can be used as A in this invention, are Li, Mg, Mn, Fe, Co, Ni, Cu, Zn and Pb. Of course, spinel-type ferrites formed by using these metal elements differ in the sensitivity to a reducing gas depending on the kind of the metal element A. However, any of these spinel-type ferrites can be used as the gas sensible material in this invention.

In the spinel-type ferrite represented by the general formula $AFe_2O_4$ that is used in this invention, even if the quantity of the metal element A deviates to some extent from the quantity defined by the above general formula, it does not matter. For example, a spinel-type ferrite in which the quantity of A is a little larger than the quantity defined by the above general formula such as $Mg_{1.3}Fe_{1.7}O_4$, can also be used in this invention. Further, a spinel-type ferrite in which a part of Fe is replaced by another element such as $MgFe_{1.5}Al_{0.5}O_4$, can be used in this invention.

In such a case, it is construed that the above slight deviation from the general formula results in partial formation of a crystal structure other than the spinel-type crystal structure or slight modification of the spinel-type crystal structure. However, the majority has substantially the spinel-type crystal structure and, therefore, such a modified ferrite can be used as a gas sensible material in this invention, though the gas sensitivity of the resulting gas sensor be lowered to some extent. Accordingly such a modified ferrite is included in the oxygen-vacant material in this invention.

Formation of a gas sensor using a spinel-type ferrite can be performed according to various methods, for example, press molding, sputtering, vacuum evaporation, ion, electroplating, plating and paste coating. A typical instance of the method for forming a gas sensor from a spinel-type ferrite will now be described.

Starting materials are weighed so as to attain a desired composition, and they are sufficiently mixed and pulverized. Then, the mixture is prefired, press-molded, and then sintered. The treatment temperatures for prefiring and sintering vary depending on the starting materials used, but in general, they are 700°–800°C. and 850°–1300°C., respectively. These temperature ranges can be broadened to some extent in some specific kinds of the metal element, A constituting the spinel-type ferrite. In general, the prefiring and sintering treatments are conducted in an oxygen-containing atmosphere or air.

The so obtained sintered product is then sliced and polished to form a thin plate having a desired thickness. Alternatively, the sintered product is pulverized again and coated together with a binder on a stem having an appropriate form.

Then, electrodes for measuring the electric resistance are formed on both the end portions of the so formed thin plate or coated film of the spinel-type ferrite. In general, fine wires of gold are attached to both the end portions of the thin plate or coated film, a gold-containing paste is coated on both the contact points, and the assembly is heat-treated at about 900°C for 15 minutes to fix electrodes.

When the so formed gas sensor is used for the measurement, it is generally maintained at 450°–550°C. and contacted with a sample gas. If the temperature of the gas sensor is lower than 450°C, the response time is prolonged, and if the temperature is higher than 550°C, the response time can be shortened but the sensitivity is lowered. Accordingly, it is generally preferred that the gas sensor be maintained at 450°–550°C at the time of measurement.

This invention will now be described in detail by reference to the following Examples that by no means limit the scope of this invention.

EXAMPLE 1

Stating materials (oxides, acetates, oxalates, nitrates, carbonates and other salts can be employed) were mixed at a prescribed mixing ratio and the mixture was prefired and sintered under conditions shown below according to the above-mentioned method to obtain a sintered product. Sintered products obtained in this manner had compositions of $MgFe_2O_4$, $NiFe_2O_4$, $ZnFe_2O_4$, $Li_{0.5}Fe_{2.5}O_4$, $PbFe_2O_4$, $MnFe_2O_4$, $CoFe_2O_4$ and $CuFe_2O_4$, respectively. As a result of the X-ray diffraction analysis, each of them was found to have a spinel-type crystal structure.

For comparison, $SnO_2$ was similarly sintered in an oxygen atmosphere to obtain a sintered product of $SnO_2$.

Each of these sintered products was sliced into long strips and they were polished to form thin plates. Then, the thin plates were heat-treated at 500°C for 24 hours in an atmosphere indicated below and the resistivity was measured at room temperature. Obtained results are shown in Table 1.

TABLE 1

| Material | Prefiring Temperature (°C) | Prefiring Time (hours) | Sintering Temperature (°C) | Sintering Time (hours) | Resistivity (Ω.cm) In oxygen | In air | In nitrogen |
|---|---|---|---|---|---|---|---|
| $MgFe_2O_4$ | 800 | 3 | 1200 | 3 | $6.2 \times 10^{12}$ | $4.8 \times 10^{11}$ | $3.3 \times 10^7$ |
| $NiFe_2O_4$ | 800 | 3 | 1200 | 3 | $1.4 \times 10^8$ | $8.8 \times 10^6$ | $9.4 \times 10^4$ |
| $ZnFe_2O_4$ | 800 | 3 | 1000 | 3 | $2.1 \times 10^{11}$ | $1.5 \times 10^{11}$ | $9.5 \times 10^7$ |
| $Li_{0.5}Fe_{2.5}O_4$ | 800 | 3 | 1000 | 3 | $3.9 \times 10^3$ | $6.0 \times 10^4$ | $1.6 \times 10^1$ |
| $PbFe_2O_4$ | 700 | 3 | 800 | 3 | $4.5 \times 10^6$ | $7.4 \times 10^8$ | $3.2 \times 10^7$ |
| $MnFe_2O_4$ | 800 | 3 | 1200 | 3 | $3.1 \times 10^4$ | $4.2 \times 10^4$ | $3.4 \times 10^3$ |
| $CoFe_2O_4$ | 800 | 3 | 1200 | 3 | $3.2 \times 10^6$ | $3.3 \times 10^6$ | $3.2 \times 10^5$ |
| $CuFe_2O_4$ | 800 | 3 | 1000 | 3 | $4.9 \times 10^3$ | $3.9 \times 10^3$ | $7.5 \times 10^2$ |
| $SnO_2$ | 1000 | 3 | 1400 | 3 | $10^{14}$ | $10^{14}$ | $10^{14}$ |

In Table 1, as the difference between the standard resistivity obtained by the heat treatment in air and the resistivity obtained by the heat treatment in either an oxidizing atmosphere (oxygen) or a reducing atmosphere (nitrogen) is greater, the sintered material has a higher sensitivity to a reducing gas.

As is apparent from the results shown in Table 1, when spinel-type ferrites are heat-treated at 500°C, the resistivity differs greatly depending on the kind of the treatment atmosphere, and it is seen that they are excellent as gas sensible materials for gas sensors. In contrast, in the case of $SnO_2$, the resistivity is $10^{14} \Omega \cdot cm$ or higher and it hardly changes depending on the kind of the treatment atmosphere.

EXAMPLE 2

$MgFe_2O_4$ and $NiFe_2O_4$ as spinel-type ferrites and $SnO_2$ as a comparison were prefired and sintered and formed into gas sensors in the same manner as described in Example 1. Each of the so obtained gas sensors was contacted at 500°C in succession with air containing 1% of propane, air, and air containing 1% of propane, and the resistivity was measured to obtain results shown in FIG. 4.

Figure 5:
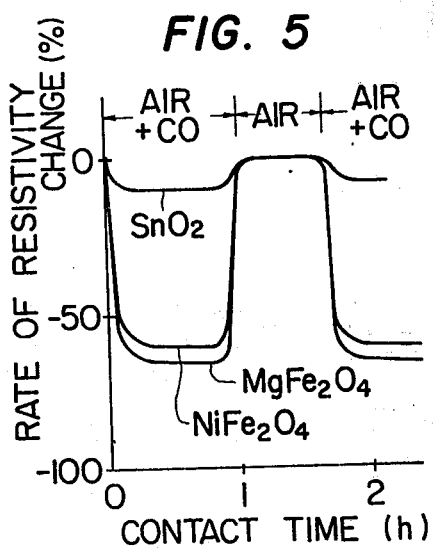

Further, each gas sensor was contacted at 500°C in succession with air containing 1% of carbon monoxide, air, and air containing 1% of carbon monoxide, and the resistivity was measured to obtain results shown in FIG. 5.

Figure 4:
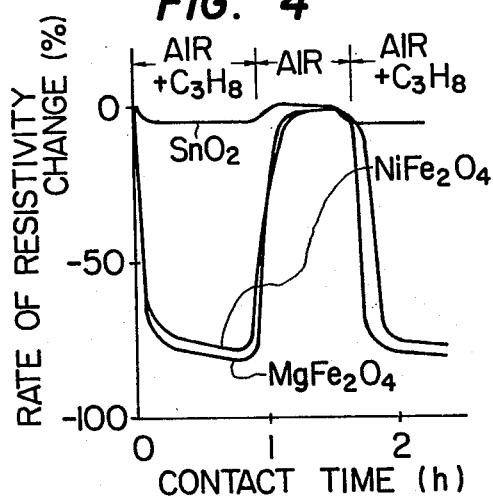
FIG. 4 and FIG. 5 are curves showing results of measuring the rates of change of the resistivity when a conventional reduction-type oxide semiconductor and a spinel-type ferrite to be used in this invention were contacted with air and a reducing gas.

Each of FIGS. 4 and 5 is a curve in which the sensitivities of the respective oxygen-vacant materials to a reducing gas are expressed in terms of the rates of change of resistivities of these materials. From these curves, it is apparent that $MgFe_2O_4$ and $NiFe_2O_4$, which are spinel-type ferrites, have higher sensitivities to propane and carbon monoxide, each of which is a reducing gas, than $SnO_2$.

EXAMPLE 3

In Example 2, the measurement was conducted with respect to the sintered material in each case. The sensitivity of the sintered material to a reducing gas can be further improved by reducing the density in the sintered material. More specifically, if the temperature adopted at the sintering step is lowered within a range capable of forming a spinel-type ferrite, the porosity is increased in the resulting sintered material and hence, the sensitivity to a reducing gas is improved.

Figure 6A:
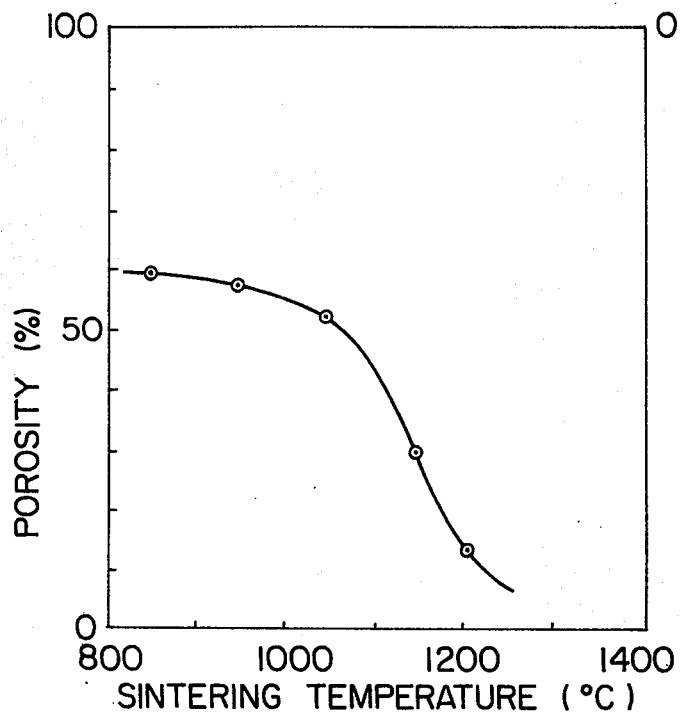
FIG. 6a and FIG. 6b illustrate the relation between the sintering temperature for forming a spinel-type ferrite and the porosity of the sintered product and the relation between the porosity and the rate of change of the resistivity.
Figure 6B:
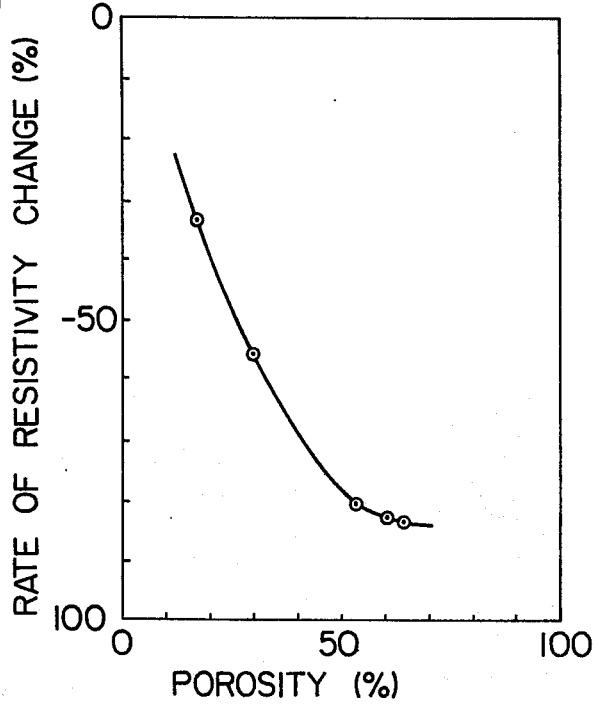

FIG. 6a illustrates the relation between the sintering temperature adopted for formation of $MgFe_2O_4$ and the porosity in the resulting sintered product, and FIG. 6b illustrates the relation between the porosity and the rate of change of the resistivity observed when the so sintered product was maintained at 500°C in an atmosphere of air containing 0.1% of gaseous propane.

As is apparent from FIG. 6a, if the sintering temperature for formation of $MgFe_2O_4$ is adjusted to about 850°C, the porosity of the resulting sintered product is about 60%, and if this sintered product is contacted with air containing 0.1% of propane, as is seen from FIG. 6b, the rate of change of the resistivity is as high as about 80%.

Results of determining the rate of change of the resistivity observed when a sintered material of $MgFe_2O_4$ formed by conducting the sintering at 950°C was contacted with air containing 0.1% of a reducing gas indicated below are shown in Table 2. From the results shown in Table 2, it will readily be understood that the sintered product of $MgFe_2O_4$ has high sensitivities to other reducing gases as well as propane.

TABLE 2

| Reducing Gas | Rate of Change of Resistivity (%) |
|---|---|
| propane | 80 |
| isobutane | 77 |
| hydrogen | 21 |
| carbon monoxide | 65 |
| alcohol | 70 |

EXAMPLE 4

Several kinds of oxides having a spinel crystal structure and oxides having other crystal structures were contacted at 500°C with air containing 0.1% of gaseous propane, and the rate of change of the resistivity were compared to obtain results shown in Table 3 on the following page.

As is apparent from the results shown in Table 3, in iron-containing spinel-type ferrites, such as $MgFe_2O_4$, $NiFe_2O_4$, $ZnFe_2O_4$ and $Li_{0.5}Fe_{2.5}O_4$, the resistivity is changed when they are contacted with propane contained in air in an amount of 0.1%. In contrast, the resistivity is not changed in the case of materials having a structure other than the spinel structure, such as $YFeO_3$, $YFe_5O_{12}$ and $LaCoO_3$ and spinel-type materials free of iron, such as $NiMn_2O_4$.

From the foregoing results, it will readily be understood that in a gas sensor for detecting a reducing gas, it is indispensable that the gas sensible material should have a spinel-type crystal structure and should contain iron.

EXAMPLE 5

The spinel-type ferrite to be used in this invention is represented by the general formula $AFe_2O_4$. Two or more metal elements can be used as A in this invention. For example, a spinel-type ferrite represented by the general formula $A_{1-x}B_xFe_2O_4$ (in which A is as defined above, B is a member selected from Li, Mg, Mn, Fe, Co, Ni, Cu, Zn and Pb, but different from A, and $x$ is a number of $0 < X < 1$) can also be used in this invention. In this case, the sensitivity to a reducing gas can be greatly changed optionally by selecting A, B and $x$ in the above general formula appropriately. Accordingly, characters suitable for the intended use can easily be obtained.

Figure 7:
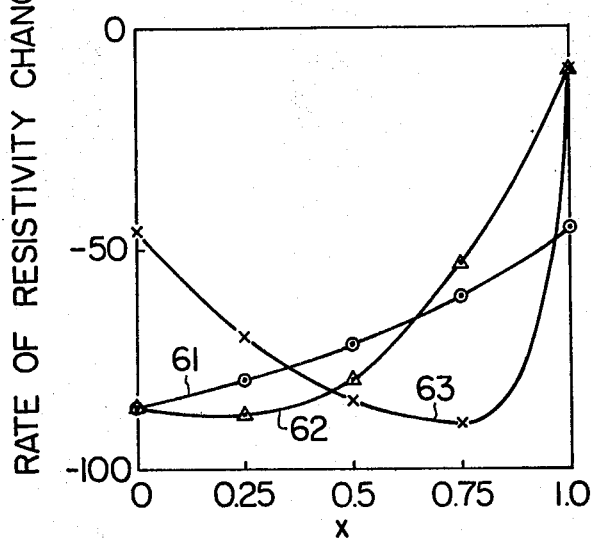
FIG. 7 and FIG. 8 illustrate the rate of change of the resistivity in spinel-type ferrites having a composition which is not included in the general formula $AFe_2O_4$.

Curves 61, 62 and 63 of FIG. 7 illustrate results of measurement of the sensitivity to 0.1% of propane contained in air, said measurement being conducted at 500°C with respect to spinel-type solid solutions $Mg_{1-x}Ni_xFe_2O_4$, $Mg_{1-x}Zn_xFe_2O_4$ and $Ni_{1-x}Zn_xFe_2O_4$ which were prepared by performing the sintering at 950°C and in which the value of $x$ was changed. From the results shown in FIG. 7, it will readily be understood that the rate of change of the resistivity is changed by the change of the value of $x$ in each solid solution of the spinel-type crystal structure. Therefore, if the value of $x$ is appropriately chosen depending on the kind of the spinel-type ferrite used and the kind and concentration of the reducing gas to be detected, a gas sensor most suitable for the intended use can be formed.

EXAMPLE 6

The spinel-type ferrite to be used in this invention is represented by the general formula $AFe_2O_4$. In this invention, however, a spinel-type ferrite in which the A/Fe atomic ratio is different to some extent from ½ can also be used without any particular disadvantage.

Figure 8:
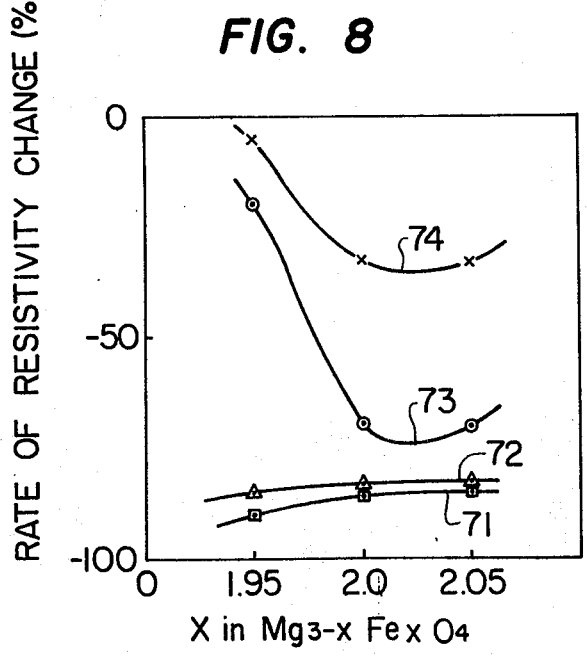

FIG. 8 illustrates the relation between the Mg/Fe atomic ratio and the rate of change of the resistivity observed when $MgFe_2O_4$ type solid solutions formed by conducting the sintering at various temperatures were contacted at 500°C with air containing 0.1% of propane. In FIG. 8, curves 71, 72, 73 and 74 show results obtained with respect to products sintered at 850°, 950°, 1050° and 1200°C, respectively.

As is seen from the results shown in FIG. 8, when the sintering temperature is high, if the Mg/Fe atomic ratio deviates from ½, the sensitivity to propane is drastically lowered, but in the materials obtained by conducting the sintering at a lower temperature, the sensitivity to propane is high and is hardly changed if the Mg/Fe ratio deviates from ½ to some extent.

Accordingly, it will readily be understood that when the sintering temperature for formation of a spinel-type ferrite is lowered within a range capable of providing a spinel-type crystal structure, even if the atomic ratio of the component elements differs from the prescribed value to some extent, lowering of the sensitivity can be prevented and a gas sensor having good properties can be obtained.

EXAMPLE 7

Another merit of the gas sensor of this invention is

TABLE 3

| Material | Prefiring Temperature (°C) | Time (hours) | Sintering Temperature (°C) | Time (hours) | Crystal Strucutre | Rate of CHange of Resistivity (%) |
|---|---|---|---|---|---|---|
| $MgFe_2O_4$ | 800 | 3 | 1200 | 3 | spinel | −33 |
| $NiFe_2O_4$ | 800 | 3 | 1200 | 3 | spinel | −15 |
| $ZnFe_2O_4$ | 800 | 3 | 1000 | 3 | spinel | −5 |
| $Li_{0.5}Fe_{2.5}O_4$ | 800 | 3 | 1000 | 3 | spinel | −3 |
| $YFeO_3$ | 800 | 3 | 1400 | 3 | perovskite | ~0 |
| $Y_3Fe_5O_{12}$ | 800 | 3 | 1400 | 3 | garnet | ~0 |
| $LaCoO_3$ | 800 | 3 | 1200 | 3 | perovskite | ~0 |
| $NiMn_2O_4$ | 800 | 3 | 1000 | 3 | spinel | ~0 | that the influence of moisture (humidity) contained in a sample gas on the sensitivity to a reducing gas is much reduced over conventional gas sensors formed by using $SnO_2$ or the like. This example illustrates this merit of the gas sensor of this invention.

$MgFe_2O_4$ formed by conducting the sintering at 850°C was powderized and the powder was mixed and kneaded with a binder comprising α-terebineol and ethylcellulose. The kneaded mixture was coated on the outer surface of a cylindrical insulator to form a gas sensor as shown in FIG. 2.

The resistivity of the so formed gas sensor as measured in air having a relative humidity of 60% at 20°C was designated as the standard resistivity. Then, the humidity was changed and the change of the resistivity was determined to obtain results shown in FIG. 9. Curve 81 of FIG. 9 shows the results obtained with respect to the gas sensor comprising the above $MgFe_2O_4$, and curve 82 of FIG. 9 shows the results obtained with respect to the gas sensor of the same structure as above except that it comprised $SnO_2$ as the gas sensible material.

Figure 9:
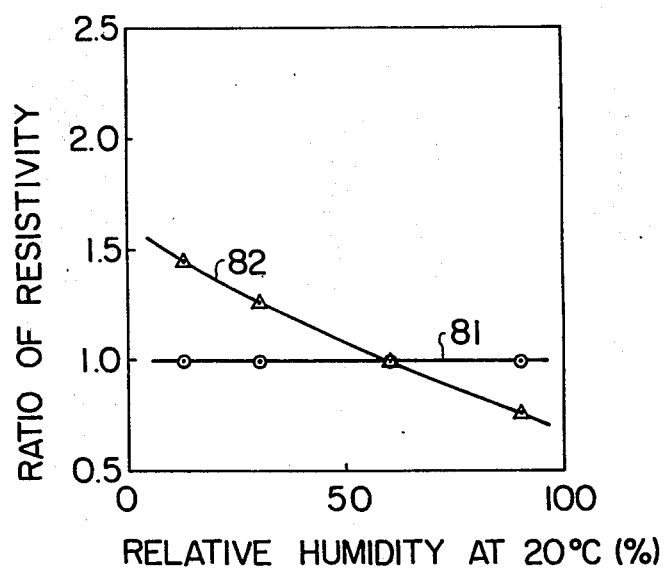
FIG. 9 is a curve illustrating the relation between the moisture content in the atmosphere and the resistivity of the gas sensor.

From the curve 81 of FIG. 9 it is seen that the resistivity of the gas sensor according to this invention is hardly changed even if the humidity is changed in a very broad range and that the detection or measurement of a reducing gas using the gas sensor of this invention is hardly influenced by moisture in a sample gas.

In contrast, as is seen from the curve 82 of FIG. 9, the resistivity of the gas sensor comprising $SnO_2$ is greatly influenced by the humidity, and as the humidity is increased, the resistivity is drastically lowered.

As is apparent from the foregoing illustration, the gas sensor of this invention is advantageous over conventional gas sensors in that incorporation of a catalyzer or recovering agent is unnecessary in many cases, products having stable characteristics can always be obtained, the sensitivity is hardly influenced by moisture in the atmosphere and hence, a high measurement reliability can be attained without fear of erroneous operations. Accordingly, this invention makes great contributions to the art.

What is claimed is:

1. A gas sensor for detection and measurement of reducing gases, which comprises a spinel-type ferrite, means for maintaining said spinel-type ferrite at a desired temperature, and means for measuring the electric resistance of said spinel-type ferrite.

2. A gas sensor as set forth in claim 1, wherein the spinel-type ferrite has a composition substantially represented by the general formula $AFe_2O_4$ in which A is at least one member selected from the group consisting of Li, Mg, Mn, Fe, Co, Ni, Cu, Zn and Pb.

3. A gas sensor as set forth in claim 1, wherein said desired temperature is within a range of from 450°–500°C.

4. A gas sensor as set forth in claim 1, wherein the reducing gas to be detected and measured is at least one member selected from hydrocarbons, hydrocarbon derivatives, alcohols, carbon monoxide, hydrogen, carboxylic acids and amines.

5. A gas sensor as set forth in claim 1, wherein said means for maintaining the spinel-type ferrite at a desired temperature acts also as means for measuring the electric resistance of said spinel-type ferrite.

6. A gas sensor as set forth in claim 1, wherein the spinel-type ferrite is coated on an insulator.

7. A gas sensor as set forth in claim 4, wherein said hydrocarbon is at least one member selected from propane, methane, butane and ethylene.

8. A gas sensor as set forth in claim 1, wherein said means for measuring the electric resistance is at least a pair of electrodes.

* * * * *